United States Patent

Taheri

[11] Patent Number: 6,099,548
[45] Date of Patent: Aug. 8, 2000

[54] APPARATUS AND METHOD FOR DEPLOYING AN AORTIC ARCH GRAFT

[76] Inventor: Syde A. Taheri, 268 Dan-Troy, Williamsville, N.Y. 14221

[21] Appl. No.: 09/123,941

[22] Filed: Jul. 28, 1998

[51] Int. Cl.[7] .................................................. A61M 29/00
[52] U.S. Cl. ............................................. 606/198; 623/1
[58] Field of Search .................................. 606/198, 194, 606/108, 192, 195; 623/1, 11, 12; 128/898, 899

[56] References Cited

U.S. PATENT DOCUMENTS

| | | | |
|---|---|---|---|
| 5,628,783 | 5/1997 | Quiachon et al. | 623/1 |
| 5,716,365 | 2/1998 | Goicoechea et al. | 606/108 |
| 5,911,733 | 6/1999 | Parodi | 606/198 |

Primary Examiner—Michael Buiz
Assistant Examiner—Vikki Trinh
Attorney, Agent, or Firm—Hodgson Russ Andrews Woods & Goodyear LLP

[57] ABSTRACT

A method and apparatus for engrafting a blood vessel comprising a thin walled graft assembly with radio opaque marker, a guide wire, a guided cartheter with proximal side openings, and a set of open end stylets. The method and apparatus provides for transarterial guidance and deployment of a graft assembly for non-surgical exclusion of aortic aneurysms. The method and apparatus provides for guiding a graft assembly over the aortic arch to the ascending aorta and for guiding a graft assembly in the thoracoabdominal arterial tree.

30 Claims, 21 Drawing Sheets

"HYDRAULIC SHEATH STYLET"

DEFLATED

INFLATED

APPARATUS AND METHOD FOR DEPLOYING AN AORTIC ARCH GRAFT

FIELD OF THE INVENTION

The present invention relates to a blood vessel engrafting system for repairing aneurysms and, more particularly, to an apparatus and, method for applying an aortic graft to exclude thoracic and thoracoabdominal aortic aneurysms.

BACKGROUND OF THE INVENTION

An aortic aneurysm is a very common deteriorating disease typically manifested by a weakening and expansion of the aorta vessel wall. Aneurysms affect the ability of the vessel lumen to conduct fluids, and may at times be life threatening when, for example, rupture of the vessel wall occurs. A standard treatment for repairing an aneurysm is to surgically remove part or all of the aneurysm and implant a replacement prosthetic section into the vessel. Such surgery, however, is generally postponed until the aneurysm has grown to a diameter greater than five centimeters. With aneurysms over five centimeters in diameter, the risk of complications is greater than the risks inherent in surgical incision and grafting of the aneurysm. Consequently, aortic aneurysms measuring greater than five centimeters in diameter, and those showing rapid increase in size, are generally surgically engrafted as a matter of course, before rupture occurs.

The standard procedure for repairing an aortic aneurysm requires one or two days of preparing the large and small intestines prior to hospitalization. The operation itself generally takes one to three hours to perform, and necessitates several units of blood for transfusion. The patient commonly remains hospitalized for several days following surgery, and requires as much as three months recuperation time before returning to work.

Moreover, there remains a significantly high rate of mortality and morbidity associated with the standard procedure. The mortality rate is as high as eight percent, while the morbidity rate includes incident complications such as blood loss, respiratory tract infections, wound infections, graft infections, renal failure, and ischemia of the bleeding intestine. The typical aortic aneurysm patient is also elderly and, therefore, less able to withstand major surgery, including anesthesia; this further influences the morbidity and mortality rates.

The repair of aneurysms located in the aortic arch or in the thoracoabdominal region introduce additional complications because of their location and the curvature of the vessels, especially around the aortic arch. Accordingly, the existing surgical techniques for repairing aneurysms in these areas are also associated with significant mortality and morbidity.

Non-surgical treatments for repairing an aneurysm include deploying a graft device at the aneurysm site via a catheter traveling through the femoral artery. Conventional tubular aortic replacement sections, however, are generally considerably larger in diameter than the femoral artery and, therefore, cannot be inserted through the femoral artery lumen to the site of the aneurysm.

Even in the more advanced aortic graft assemblies which enable percutaneous deployment and placement of a spring loaded graft for a non-surgical correction of an aortic aneurysm, the required entry profiles require at least 10–12 FR. This is the case because these graft systems are comprised of graft material, two or more spring stents, a balloon catheter, a sheath introducer, and plunger at a minimum, for deployment of the graft.

Consequently, there have been efforts to design smaller devices for the non-surgical techniques to facilitate percutaneous entry and movement of the graft assembly through the arteries. Another important factor is the ability of the interventionist to control the graft assembly during the procedure. If the graft assembly is not deployed correctly, it may not make a proper seal, other problems may occur and the procedure may have to be repeated. Thus, reducing the size of the graft assembly and improving control over the graft assembly during deployment are both important factors for improving the non-surgical procedures.

For the thoraco and thoracoabdominal arterial trees, the curvature and shape of the arteries create a heightened need for control over deployment and positioning of the grafts.

Accordingly, what is needed is an improved apparatus and method for percutaneous deployment and placement of a graft in the thoracic and thoracoabdominal arterial tree.

SUMMARY OF THE INVENTION

The apparatus and method of the present invention solves the above described needs by allowing interventionists using non-surgical techniques, with percutaneous deployment and positioning of grafts, to guide a graft to the desired location in the thoraco and thoracoabdominal arterial tree. The apparatus comprises a thin walled graft with a radio opaque marker, a guide wire, a guided catheter with proximal side openings, and a set of open end stylets.

For repairing an aortic arch aneurysm, the method comprises the steps of placing the patient under general anesthesia and exposing and controlling the femoral artery, the left and right brachial arteries, and the left carotid artery. After heparinization and arteriotomy, guide wires are passed into each exposed artery and are retrieved into the groin through the femoral artery. The aortic arch graft is prethreaded with long strings that loop through openings in each branch. The strings are tied to each of the guide wires through an eyelet or loop attached to the guide wire. The guide wire is then pulled through the brachiocephalic arteries until the guide strings are retrieved. At this point, the guide wire extends through both the brachiocephalic artery and the femoral artery, and the strings also extend from the brachiocephalic arteries to the femoral artery. In this manner, the graft assembly can be guided from either end in both directions. The graft assembly also includes stylets which are attached on the inside and the outside of the graft assembly through openings in the graft or through a special catheter.

Next, the aortic arch graft is brought to the branches of the aortic arch by means of the strings. The proximal portion of the aortic arch graft is guided to the ascending aorta by forward movement of the stylet to the desired location. Once the graft is positioned by means of the strings and the stylets, the stents are passed over the central guide wires and deployed to the location of the graft in the ascending aorta. The branches of the graft are brought to each of the respective branches of the aorta and are stented into the arterial wall. Finally, the distal end of the aortic arch is stented to the descending aorta.

For thoracoabdominal aneurysms, a similar procedure is performed, however, insertion of the guide wire to the celic, superior mesenteric, and renal arteries is required prior to the introduction of the graft and the stent deployment.

Accordingly, it is an object of the present invention to provide an apparatus and a method for transarterial guidance of grafts into desired locations in the aortic arch and the thoracoabdominal arterial branches.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures.

DESCRIPTION OF THE PREFERRED EMBODIMENTS

The terms distal and proximal are used in this application and are to be understood to indicate position relevant to the heart with proximal indicating a position closer to the heart and distal indicating a position farther away from the heart.

Figure 1:
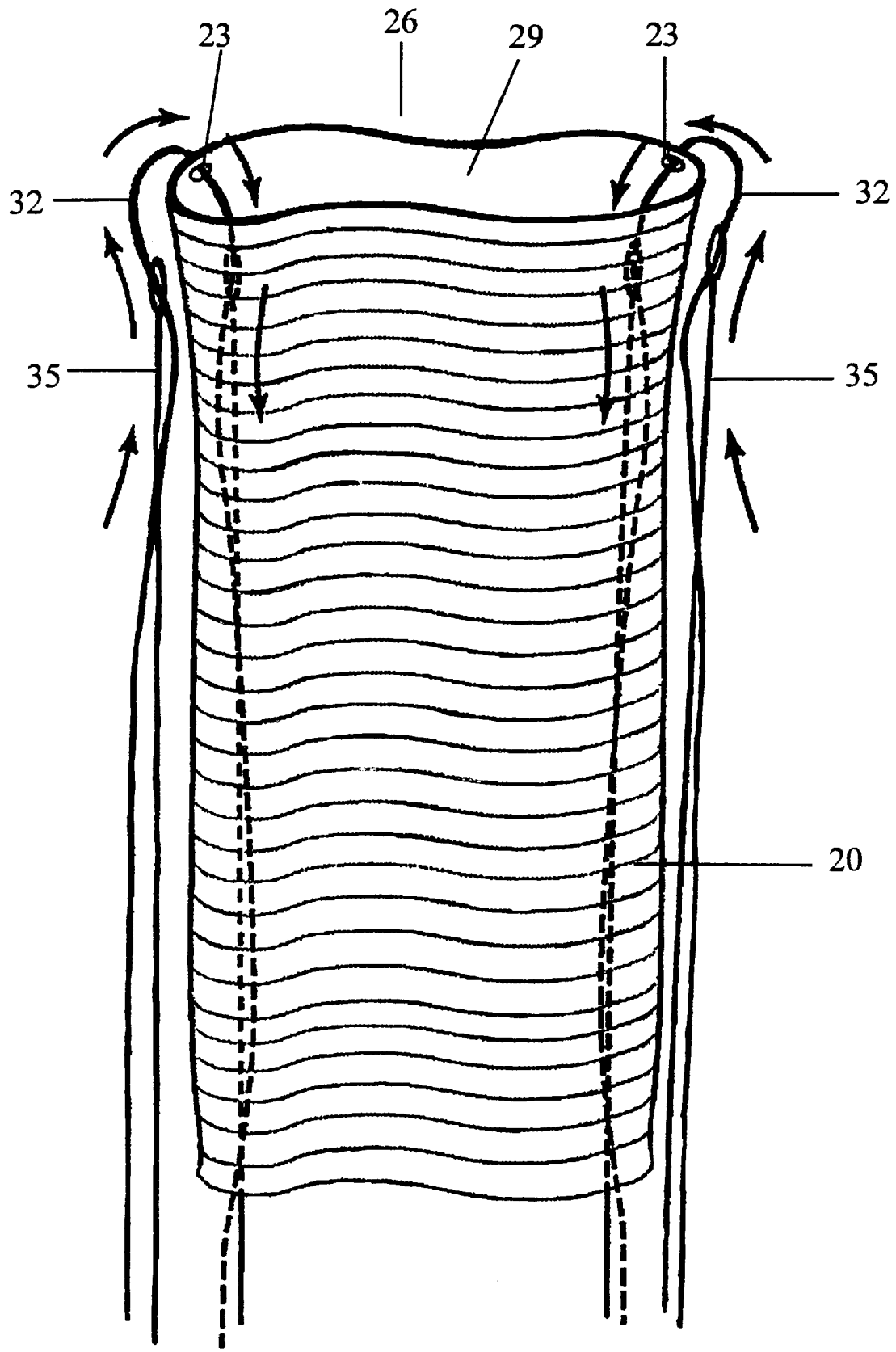
FIG. 1 is a partial perspective view of a graft assembly of the present invention.

In FIG. 1 a thin walled graft 20 has a plurality of openings 23 disposed at the proximal end 26. The graft 20 is preferably constructed of dacron.

The graft 20 takes a tubular shape when in an expanded position, but is capable of being folded or twisted for loading into a sheath introducer (not shown). Graft 20 is shown in a partial view in FIG. 1 and is best shown in its entirety in FIGS. 14 and 15. The proximal end 26 has even end portions. However, the graft 20 may be constructed with different end configurations. A plurality of strings 32 are looped through the openings 23 in end the proximal and the graft 20. The strings 32 are also threaded through stylets 35. The stylets 35 may be rigid or they may be inflatable (shown in FIGS. 3a and 3b). It is preferable to have a stylet 35 on the inside of lumen 29 and another stylet 35 on the outside of lumen 29 on each side of the graft in order to provide the best control of the graft 20 during deployment.

Figure 2:
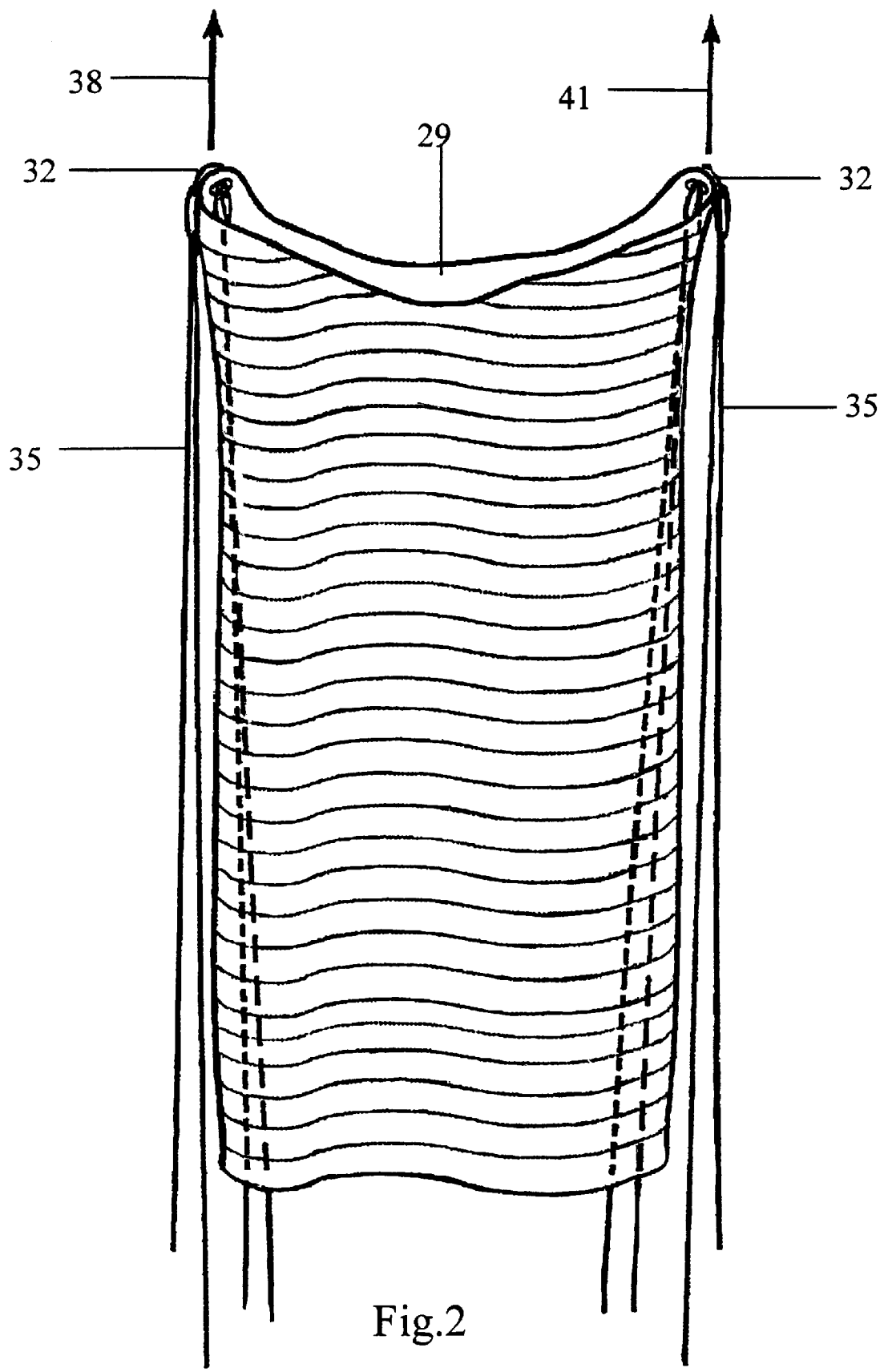
FIG. 2 is a partial perspective view of a graft assembly of the present invention being moved forward by the stylets.

Turning to FIG. 2, arrows 38 and 41 indicate the direction of travel of the graft 20 during deployment. The stylets 35 assist in moving the graft 20 to the proper location inside the arterial branches and are especially useful in positioning the graft 20 over the aortic arch into the ascending aorta. The threaded string 32 provides an attachment point for both of the stylets 35 on each side of the lumen 29. In this manner, the stylets 35 can be used to move and position the graft 20 and can easily be detached from the graft 20 along with the strings 32 once the graft 20 has been deployed. It is also important that the strings 32 and the stylets 35 assume a minimal cross-sectional area in order to facilitate entry into and movement through the arterial branches.

Figures 3A, 3B:
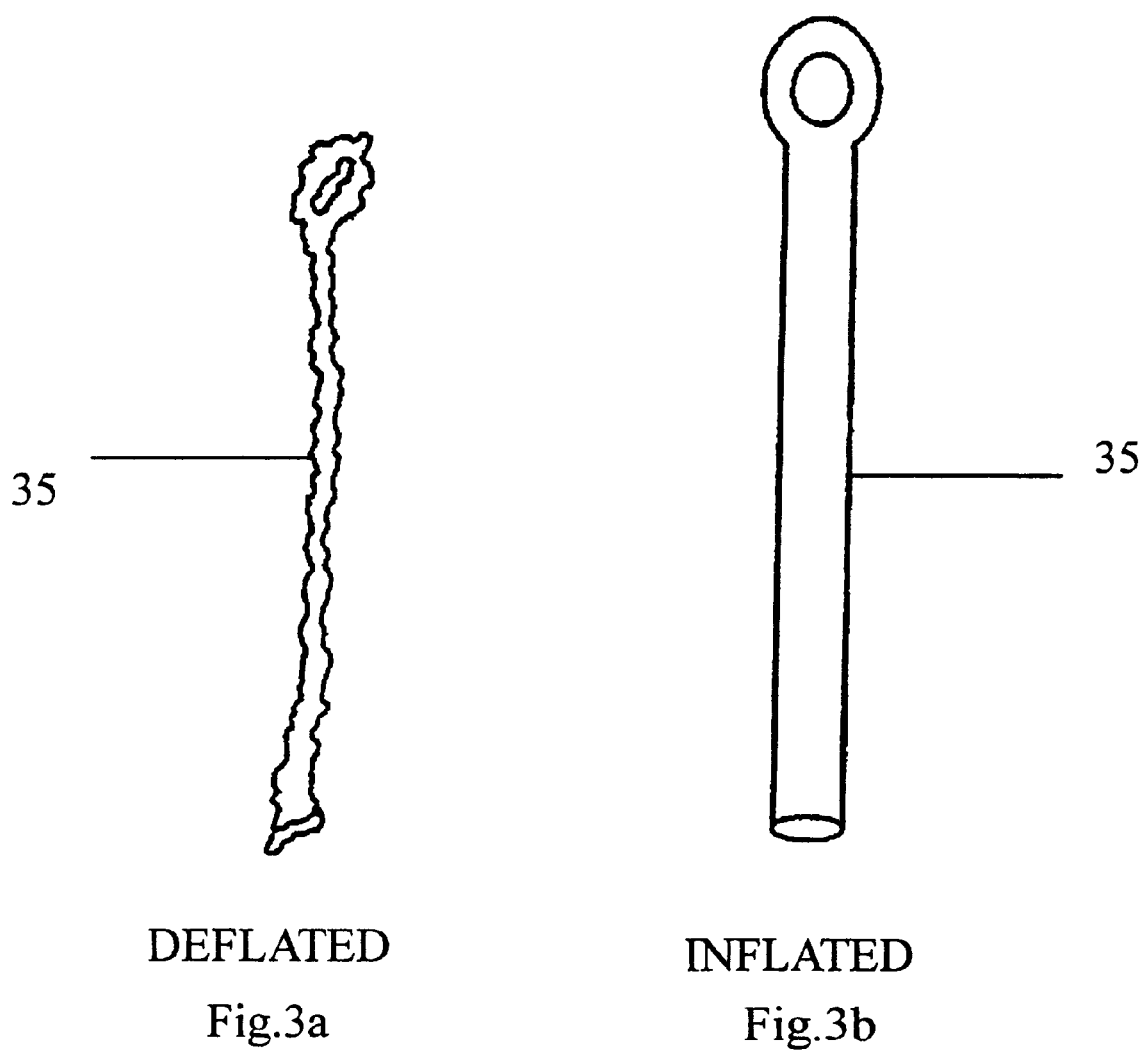
FIG. 3a is a perspective view of an alternate embodiment of the stylets of the present invention in a non-deployed condition.
FIG. 3b is a perspective view of an alternate embodiment of the stylets of the present invention in a deployed condition.

In FIG. 3a an alternate embodiment of the stylet 35 is shown in a non-deployed state. The stylet 35 is elongate, hollow, and inflatable. The inflatable stylet 35 is preferably made of a thin wall prosthetic material. When the stylet 35 is deflated it is very thin and takes up less cross-sectional area. Accordingly, it is very useful in minimizing damage to the arterial wall during deployment of the graft 20.

Turning to FIG. 3b, once the graft 20 is deployed into the larger arteries, the stylet 35 can be inflated preferably to a diameter of approximately one millimeter by injecting a fluid into the hollow interior of the stylet 35.

Figure 4:
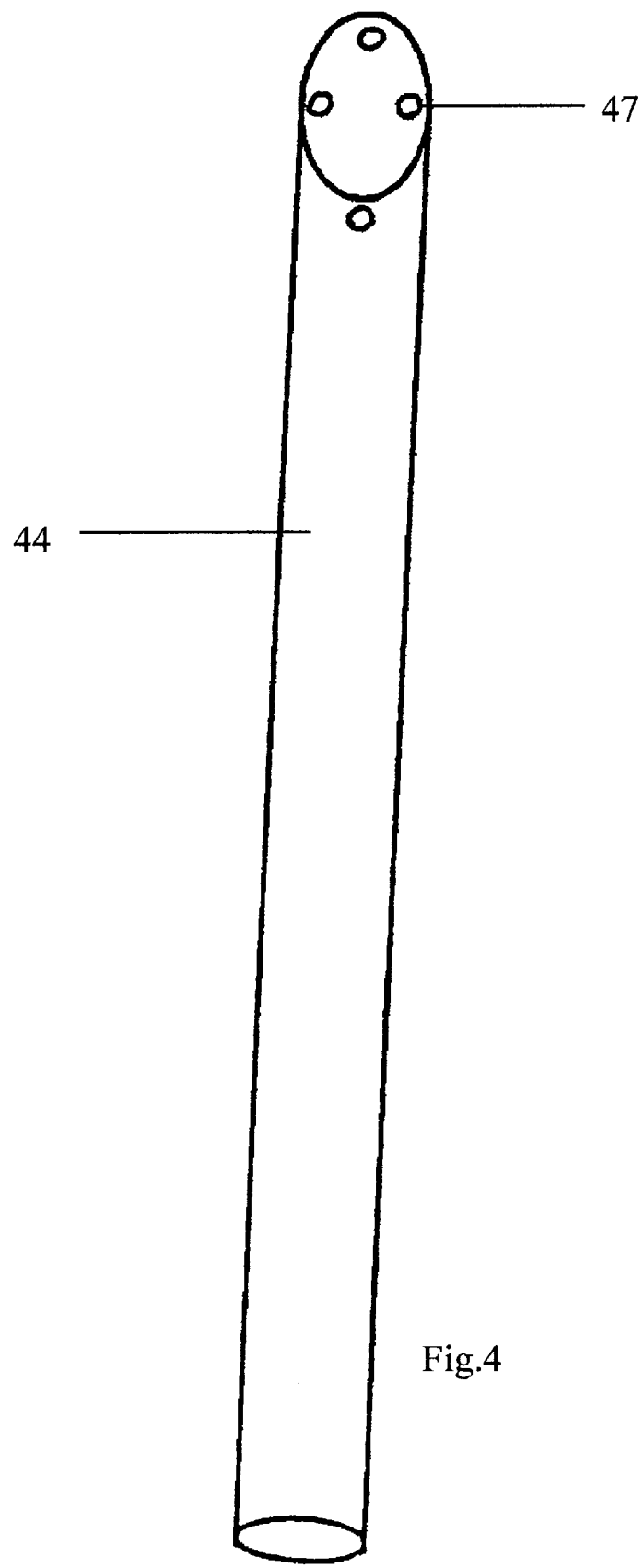
FIG. 4 is a perspective view of a perforated catheter of the present invention.

In FIG. 4 a catheter 44 is shown having a plurality of proximal openings 47. The catheter 44 provides an alternative to the stylets 35 disposed on the inside and outside of lumen 29. The catheter 44 replaces the stylets 35 positioned inside the lumen 29. The strings 32 that are normally threaded through the stylets 35 on the inside of the lumen 29 are threaded through the proximal openings 47 on catheter 44 (best shown in FIG. 5).

Figure 5:
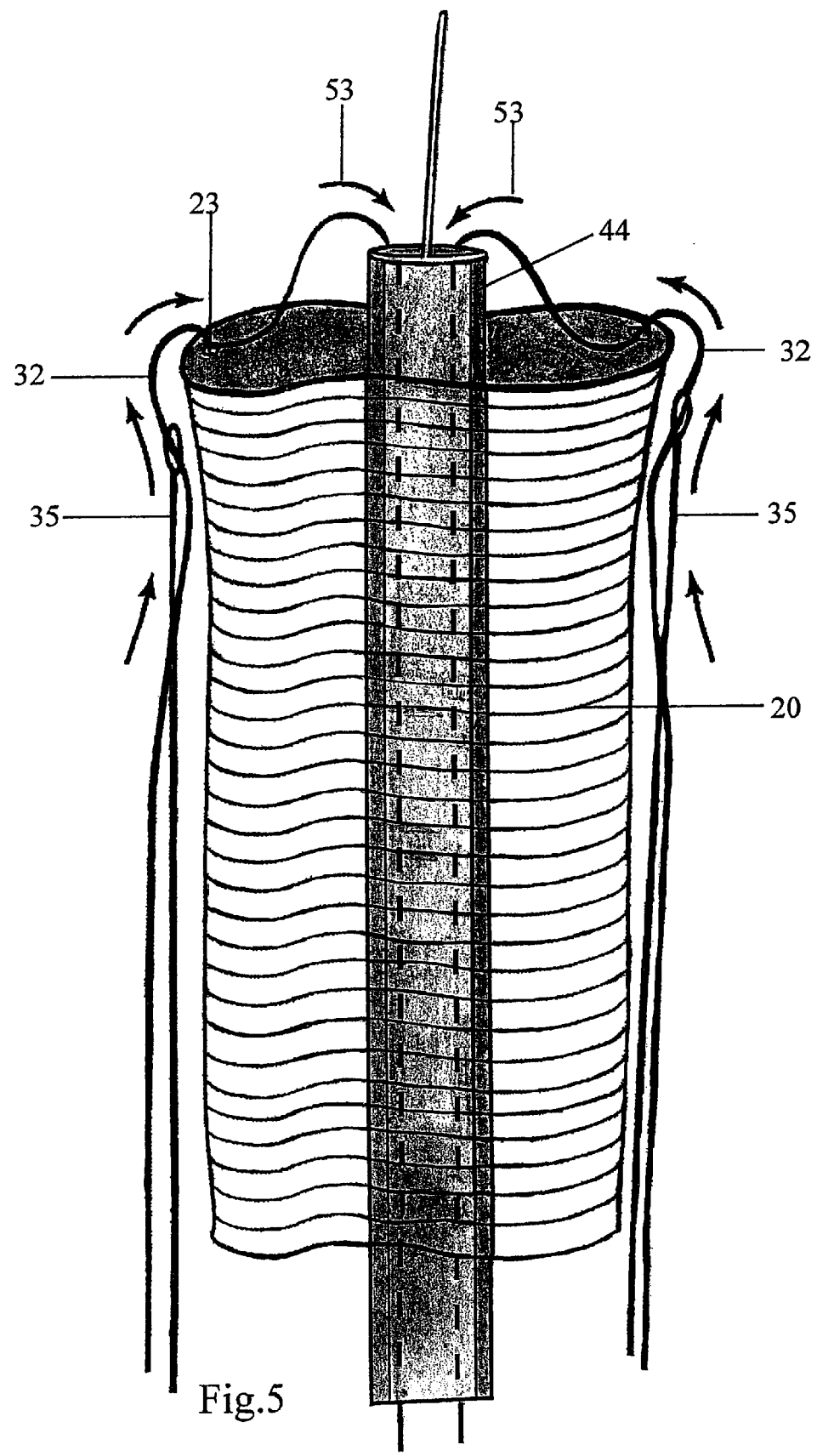
FIG. 5 is a partial perspective view of an alternate embodiment of the graft assembly of the present invention.

Turning to FIG. 5, an alternate graft assembly 50 has a plurality of strings 32. The strings 32 are threaded through stylets 35 and into catheter 44, as indicated by the directional arrows 53. Intermediate the stylet 35 in catheter 44 the strings 32 pass through openings 23 in the graft 20. Also a guide wire 56 is threaded through the proximal openings 47 in the catheter 44.

Figure 6:
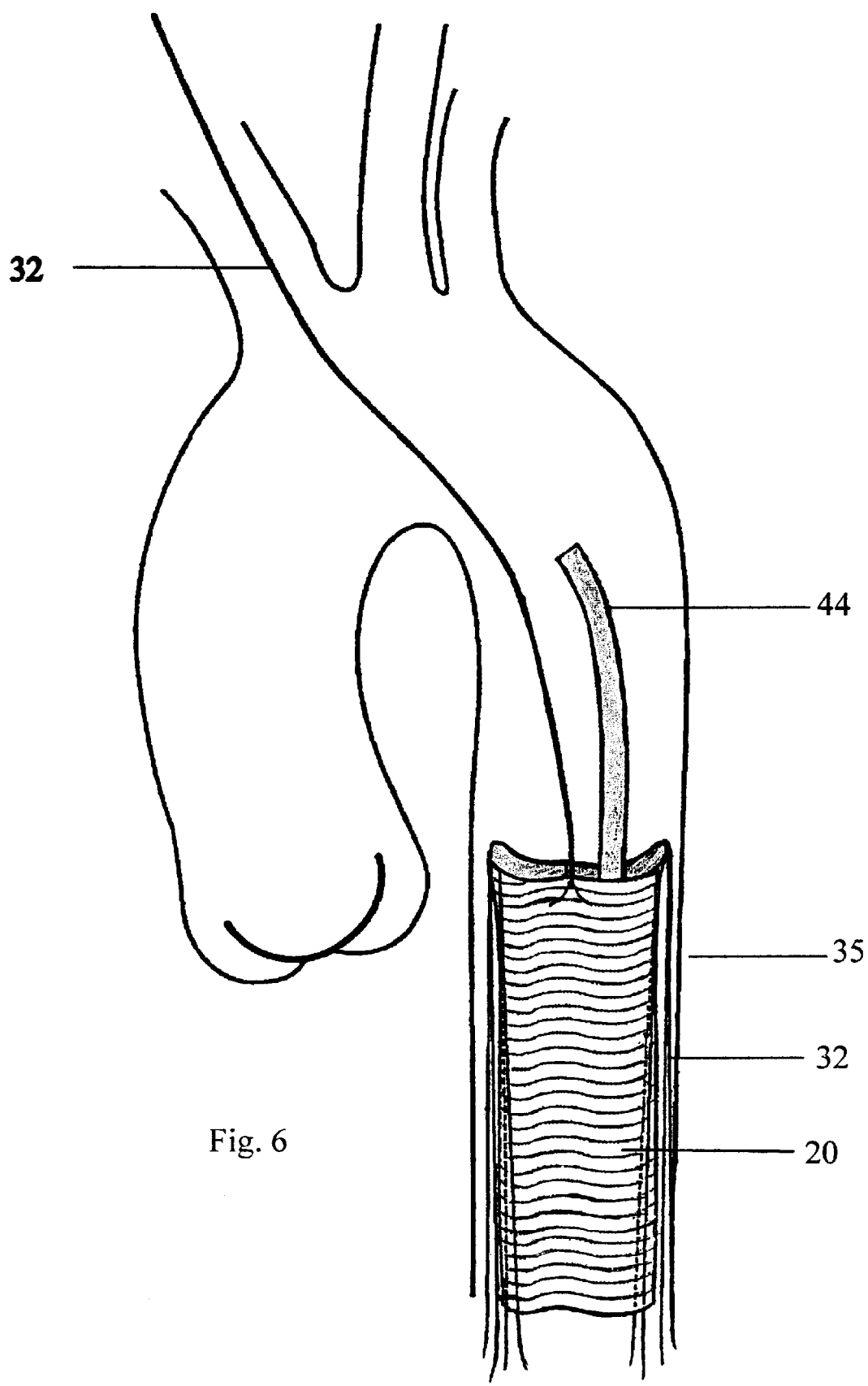
FIG. 6 is a partial perspective view of the graft assembly of the present invention being conveyed by a string toward one of the brachiocephalic arteries.

In FIG. 6 the graft 20 with strings 32 and stylets 35 is being deployed into the aortic arch area. String 32 extending from the carotid artery is used to pull the graft 20 up towards the aortic arch.

Figure 7:
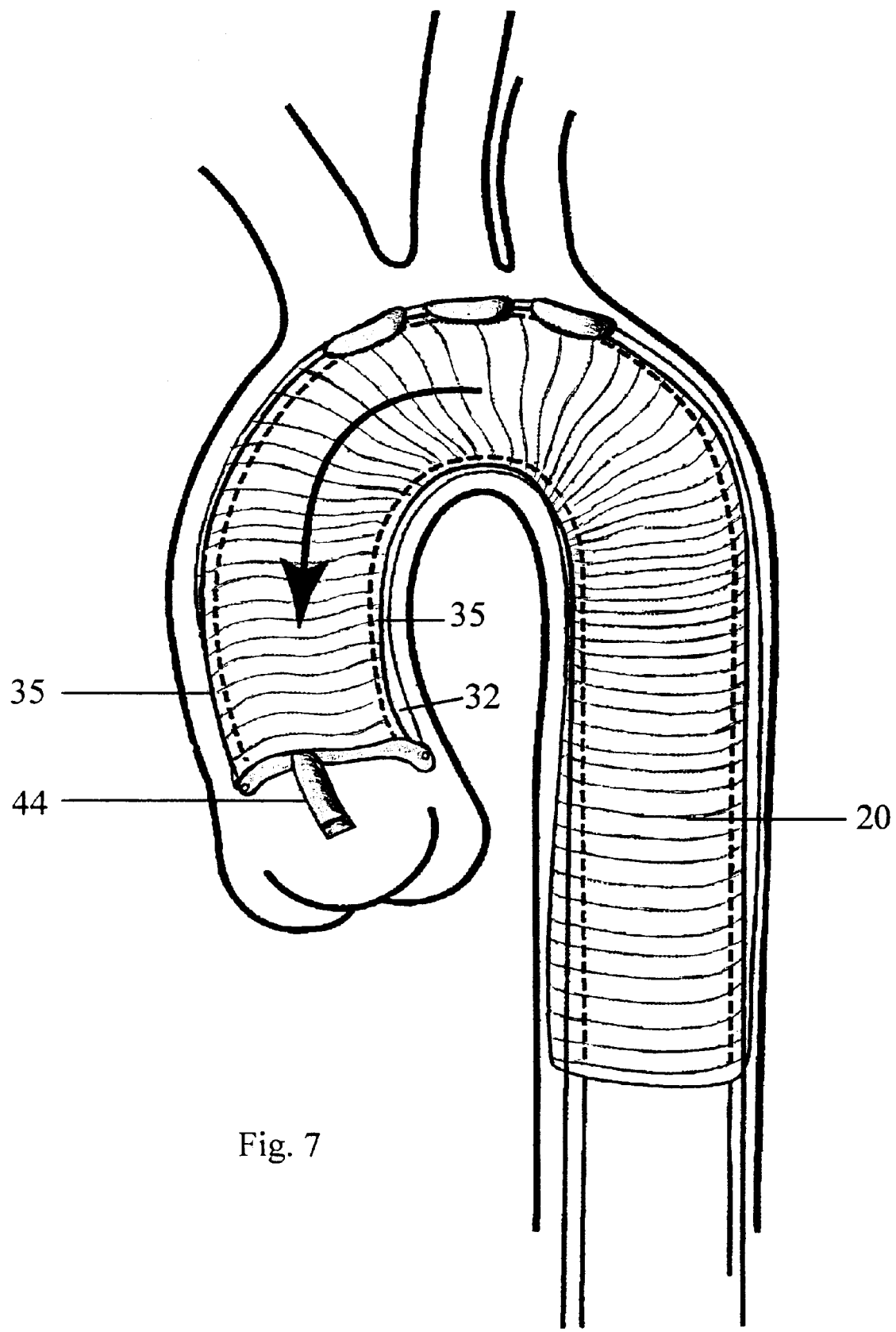
FIG. 7 is a partial perspective view of the graft assembly of the present invention being pushed forward to the ascending aorta by means of the stylets.

Turning to FIG. 7, once the graft 20 reaches the top of the aortic arch, the string 32 from the carotid artery is no longer used and the graft 20 is pushed over the arch and down to ascending aorta by the stylets 35.

Figure 8:
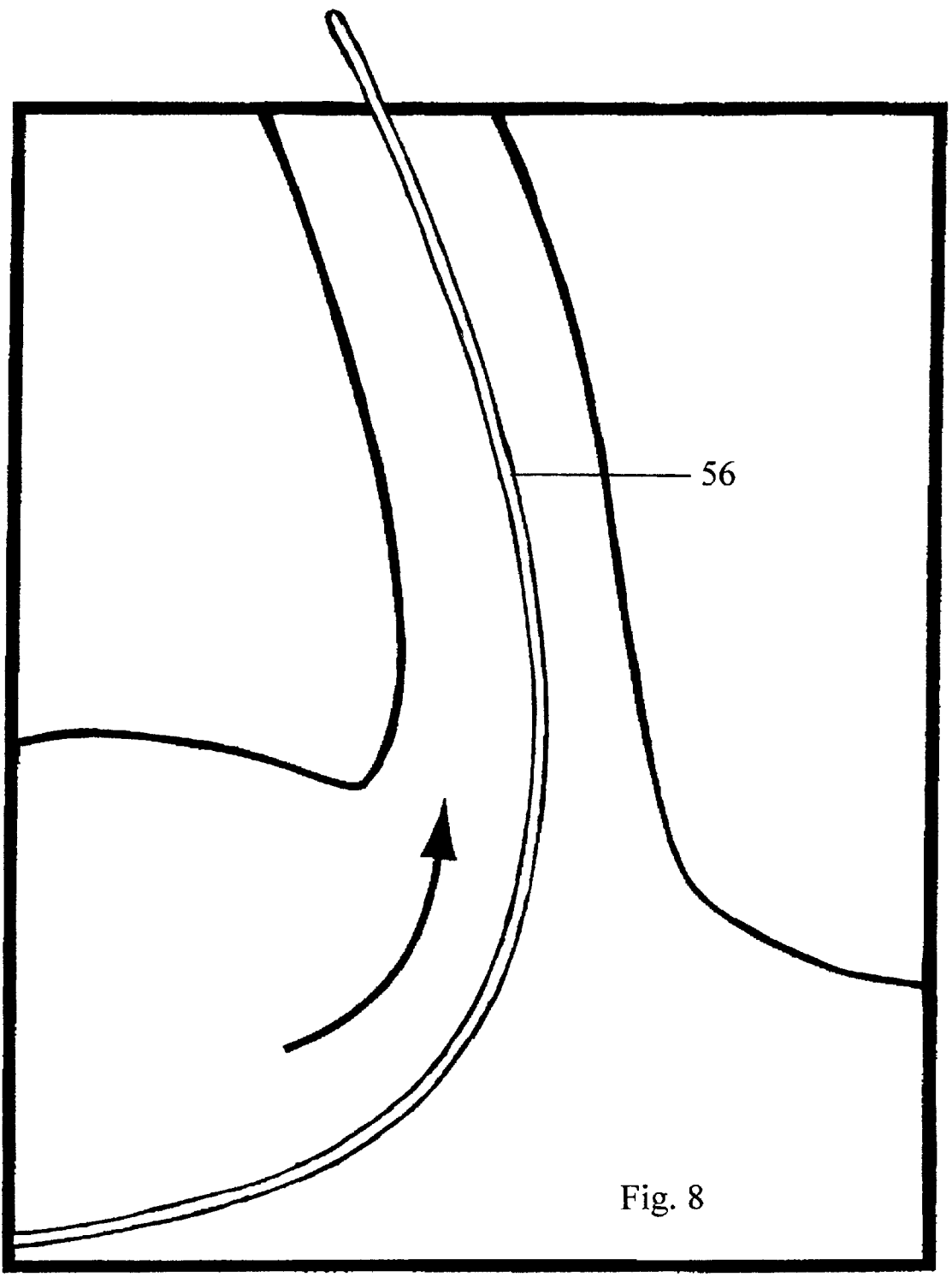
FIG. 8 is a partial perspective view of a guide wire.

FIG. 8 shows a guide wire 56 threaded through a branch of the aorta.

Figure 9:
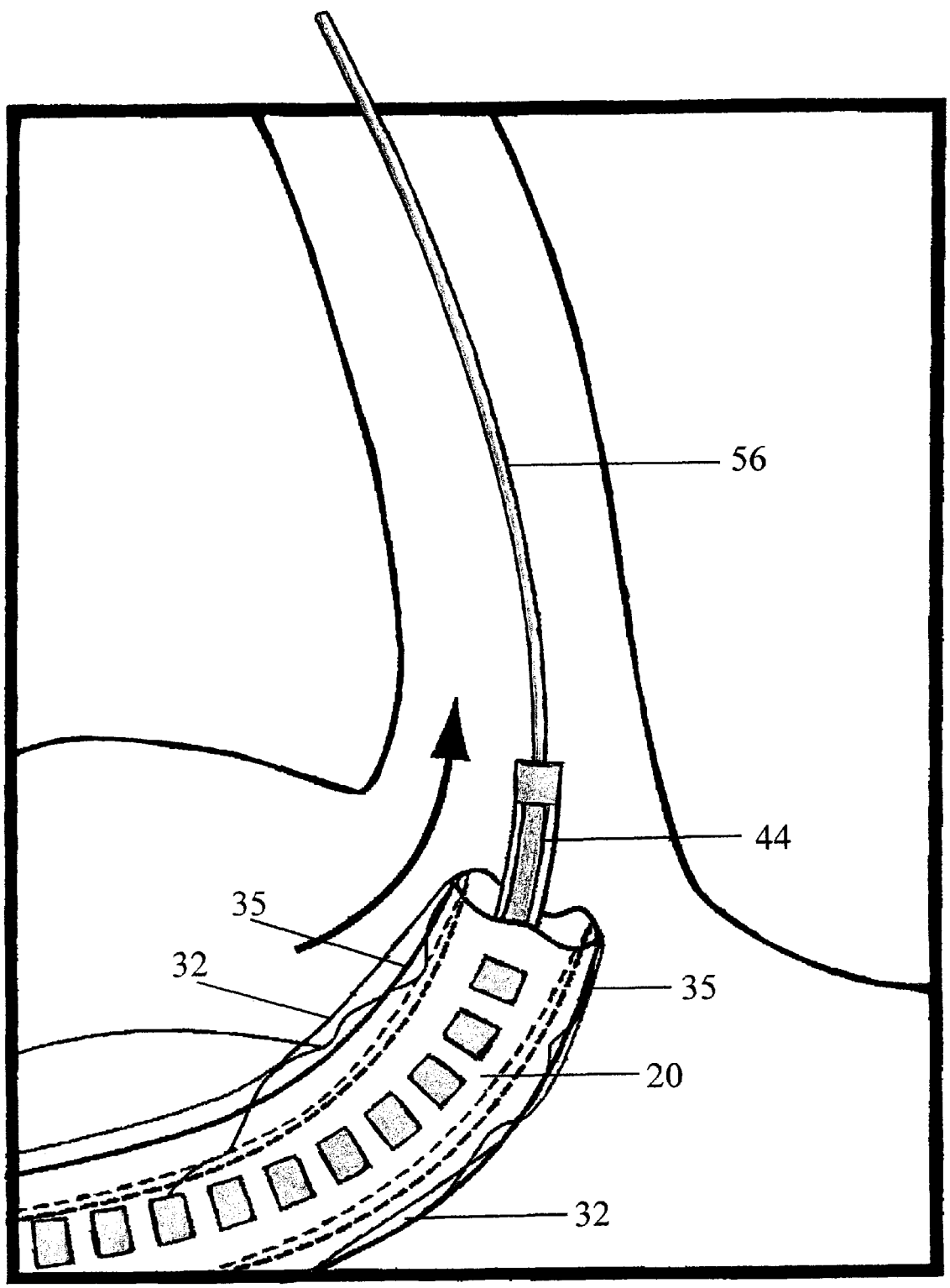
FIG. 9 is a partial perspective view of the guide wire, catheter, graft, and stylet of the present invention.

In FIG. 9 graft 20 is being moved towards the branches of the aorta by stylets 35, strings 32, and catheter 44. The catheter 44 is guided by guide wire 56.

Figure 10:
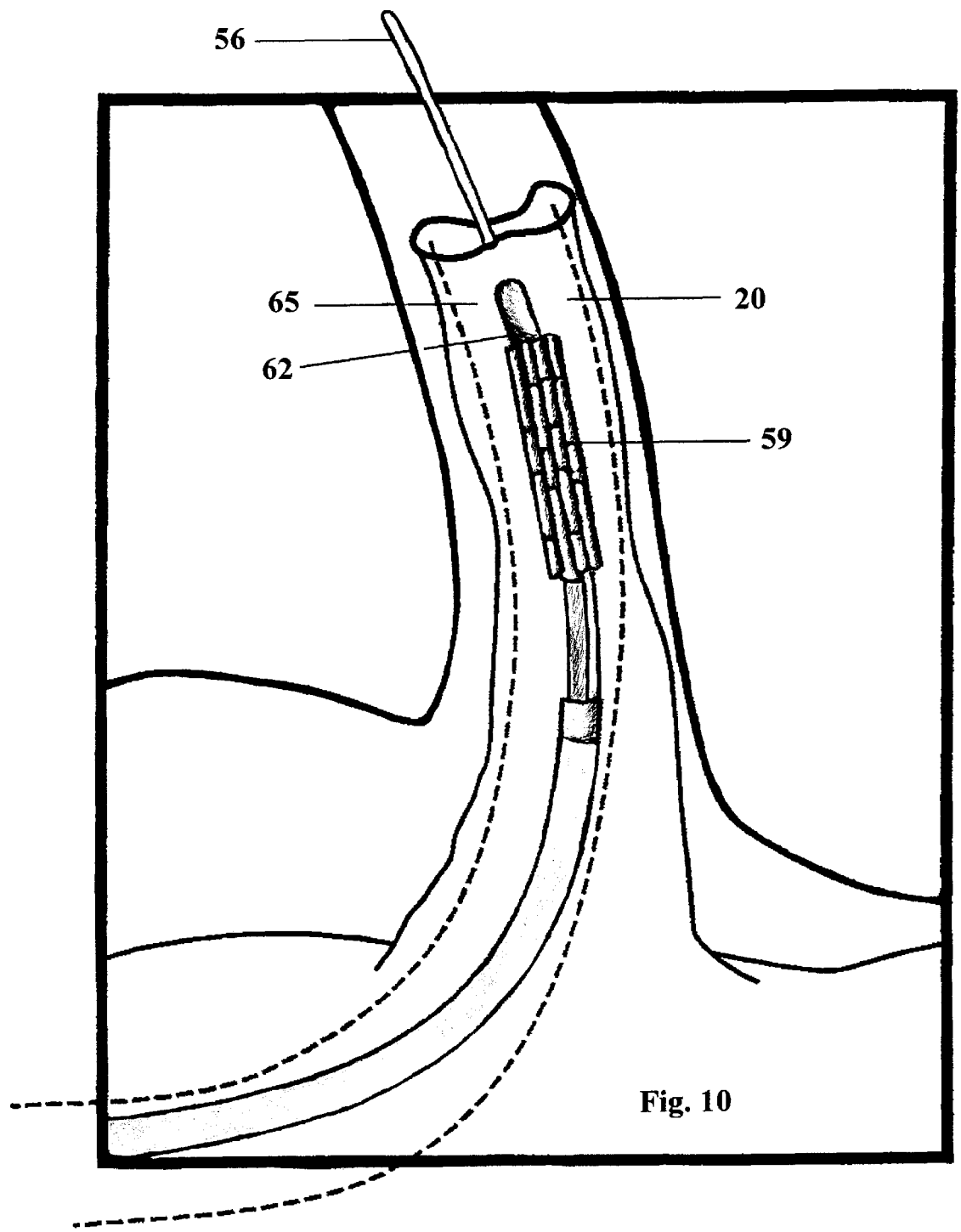
FIG. 10 is a partial perspective view of the guide wire, catheter and stent in the branches of the aorta.

Turning to FIG. 10, the graft 20 is positioned in a branch of the aorta as determined by guide wire 56. Stent 59 is deployed by a stent catheter 62. Stent 59 is preferably comprised of a material such as a metal which is deformable and capable of returning to its original shape, preferably a shape memory alloy having stress-induced martensite characteristics, such as nitinol. Other materials may also be used such as stainless steel. In operation, stent 59 is deformed either by inducing stress or in the case of a shape memory alloy not having stress induced martensite characteristics reducing temperatures sufficiently to reach the temperature threshold for the metals martensitic phase. After deformation of stent 59 it is loaded within a sheath introducer (not shown).

Stent 59 is preferably deployed by a balloon catheter 62. Prior to deformation, the stent 59 is preloaded within the sheath introducer then loaded with a balloon catheter 62. Balloon catheter 62 is comprised of a catheter having a proximal end 65 and a distal end (not shown).

Figure 11:
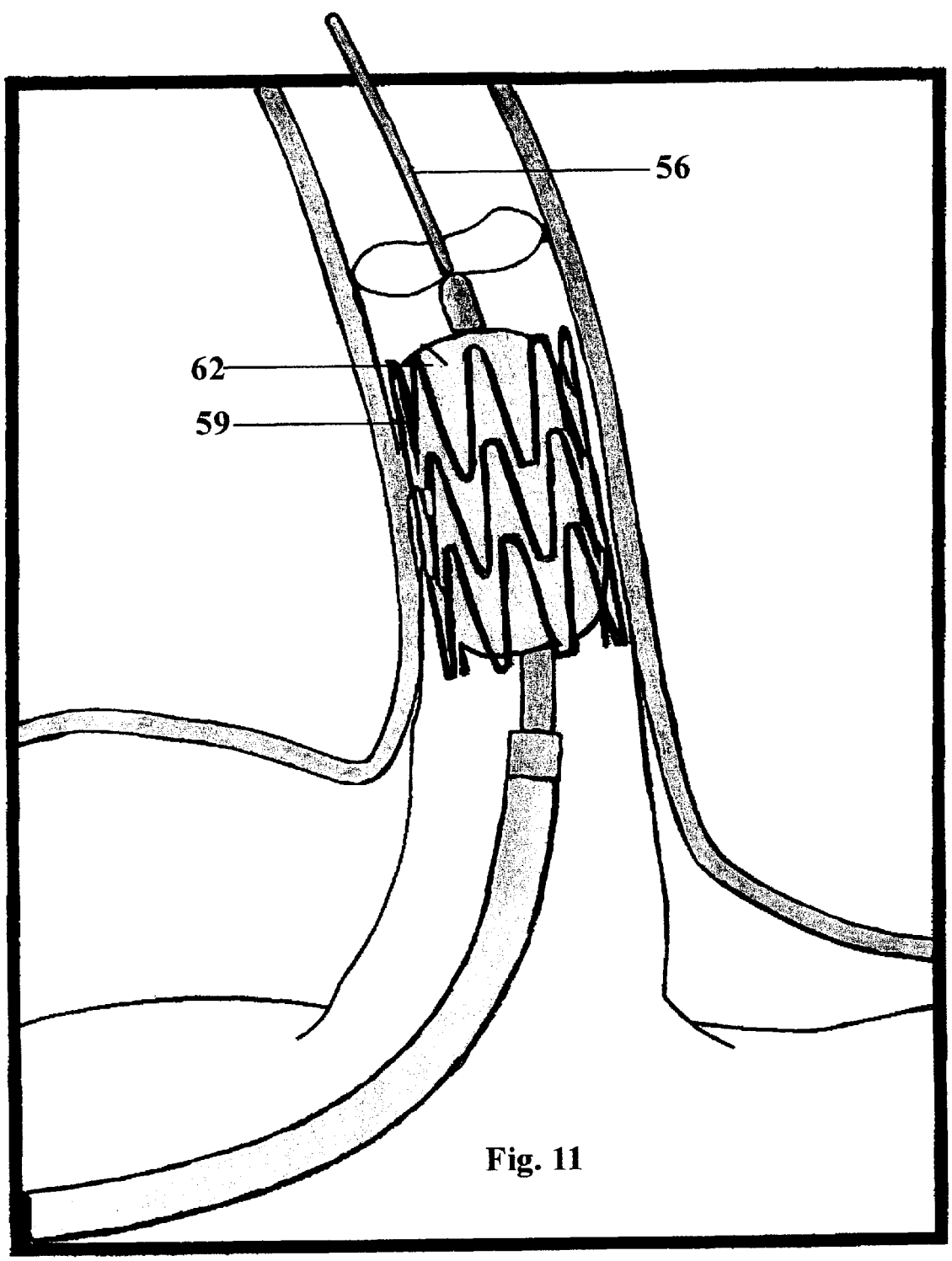
FIG. 11 is a partial perspective view of a stent being deployed in the aortic branch.
Figure 12:
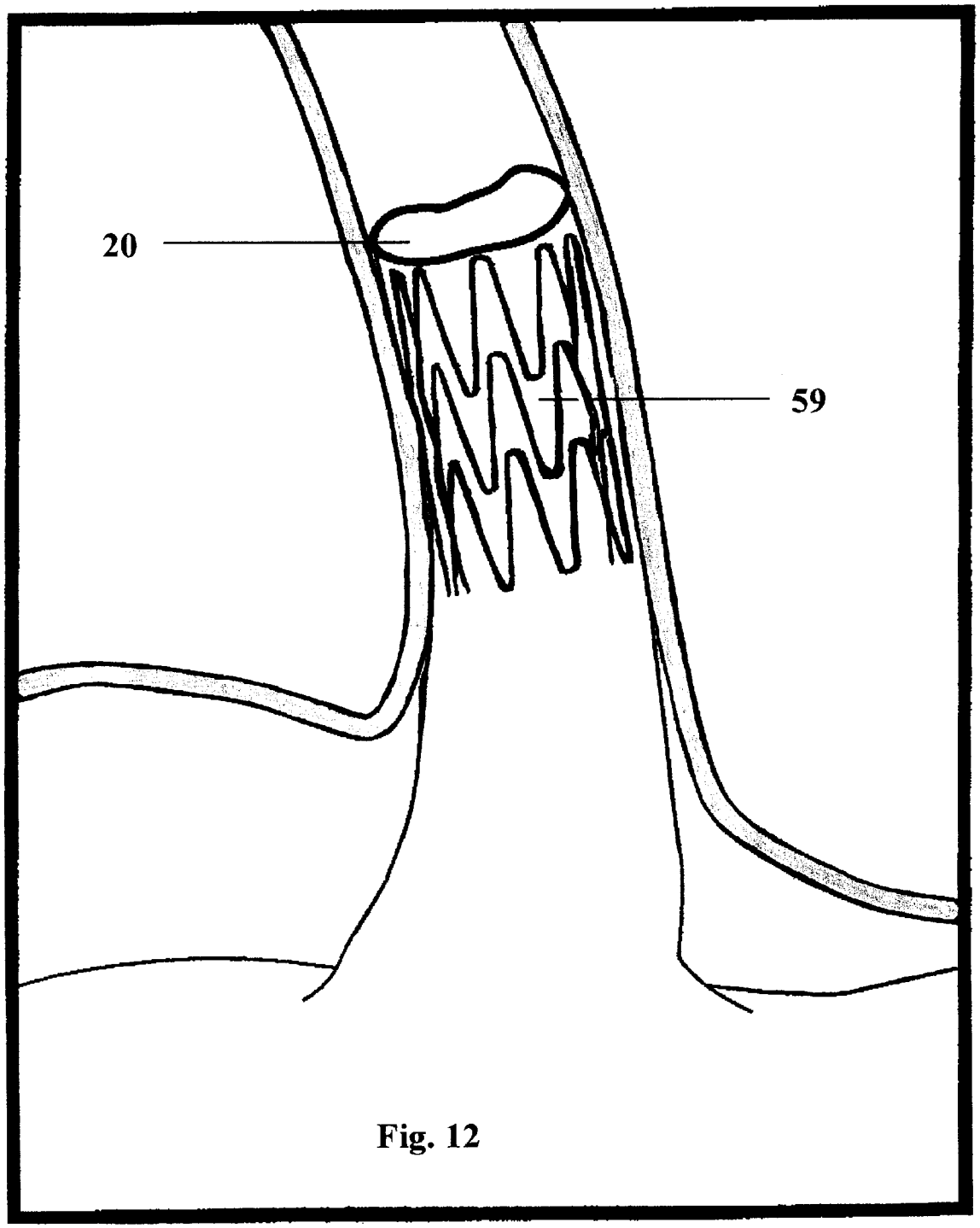
FIG. 12 is a partial perspective view of a stent deployed in the lumen of the arterial branch.

FIG. 11 shows the positioning of balloon catheter 62 to deploy stent 59 into graft 20. Turning to FIG. 12, stent 59 is shown deployed into graft 20 with the guide wire 56 and catheter 62 removed.

Figure 13:
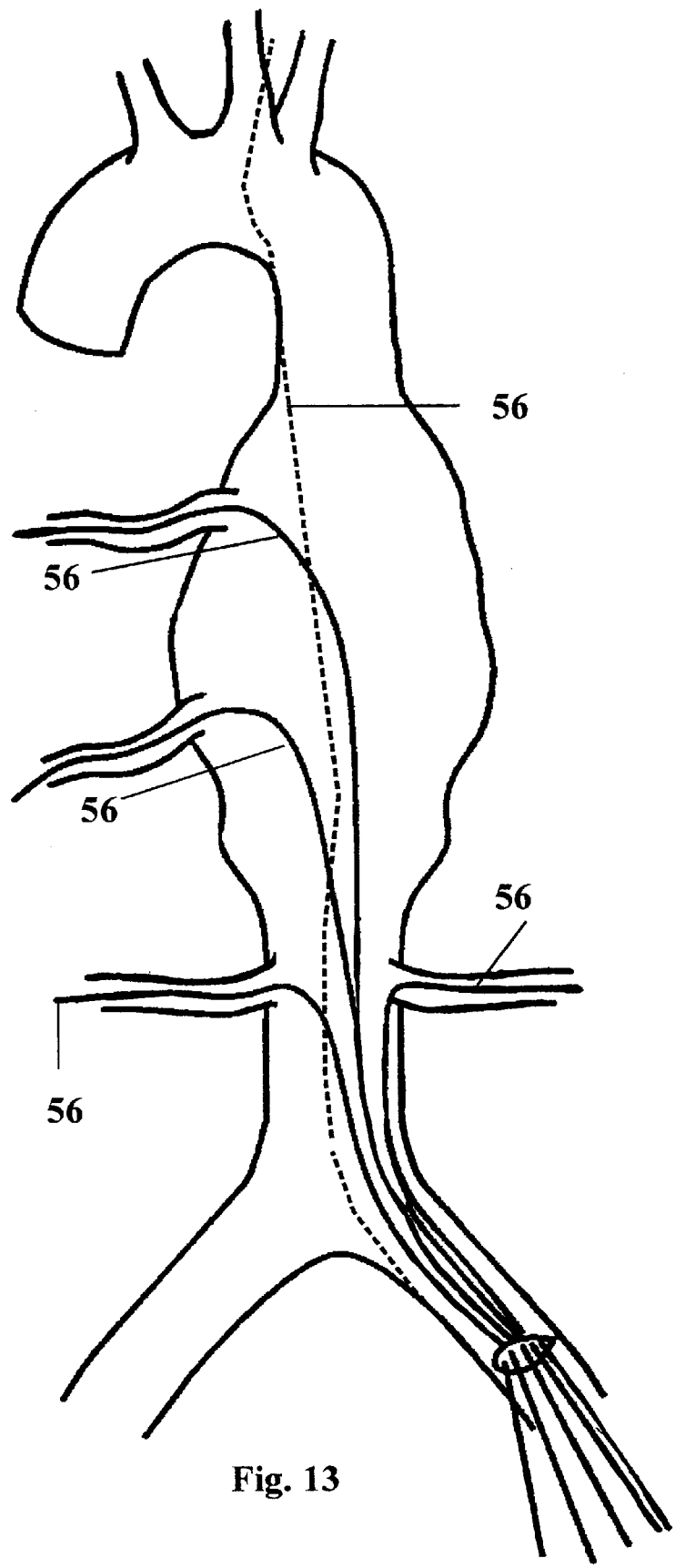
FIG. 13 is a perspective view of the guide wires inserted through the brachiocephalic arteries and retrieved through the femoral artery.
Figure 14:
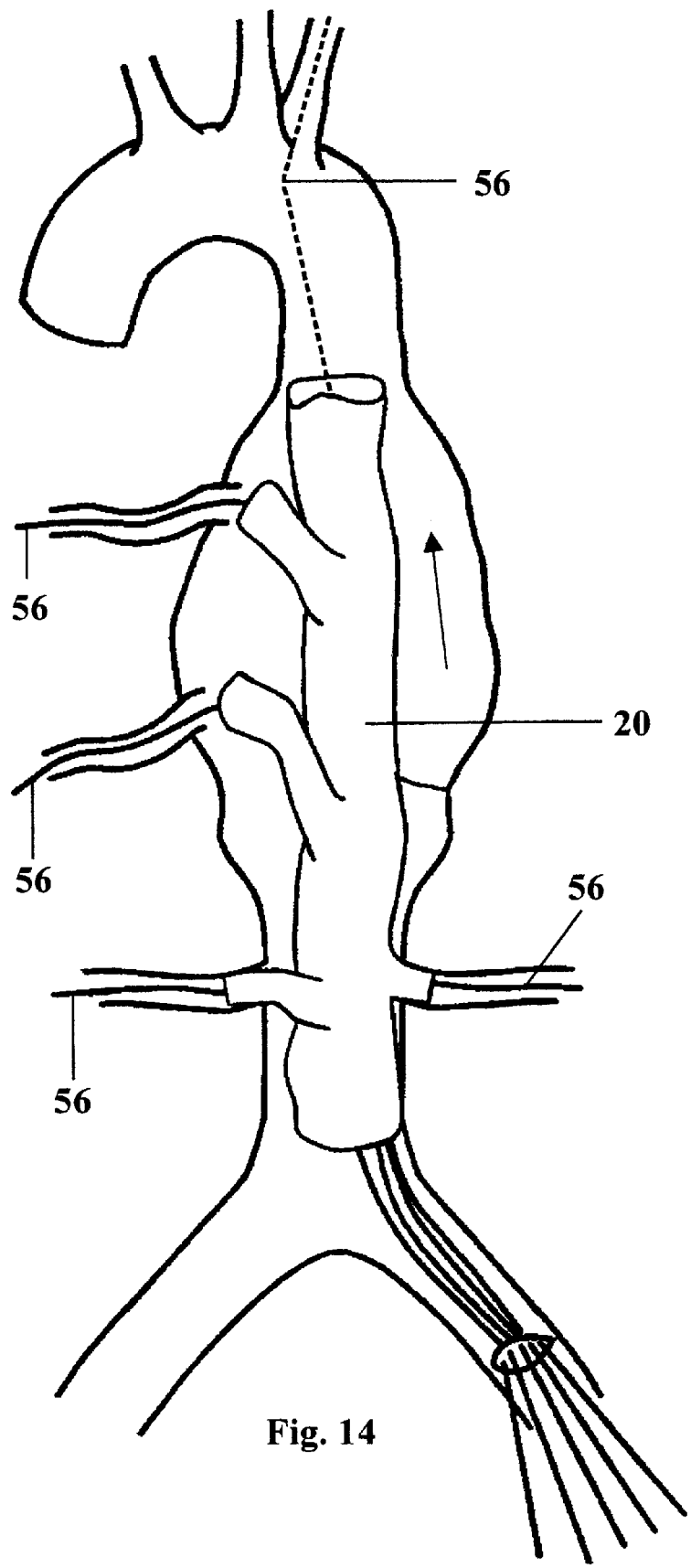
FIG. 14 is a perspective view of the branches of the aortic graft being directed toward the branches of the aorta.
Figure 15:
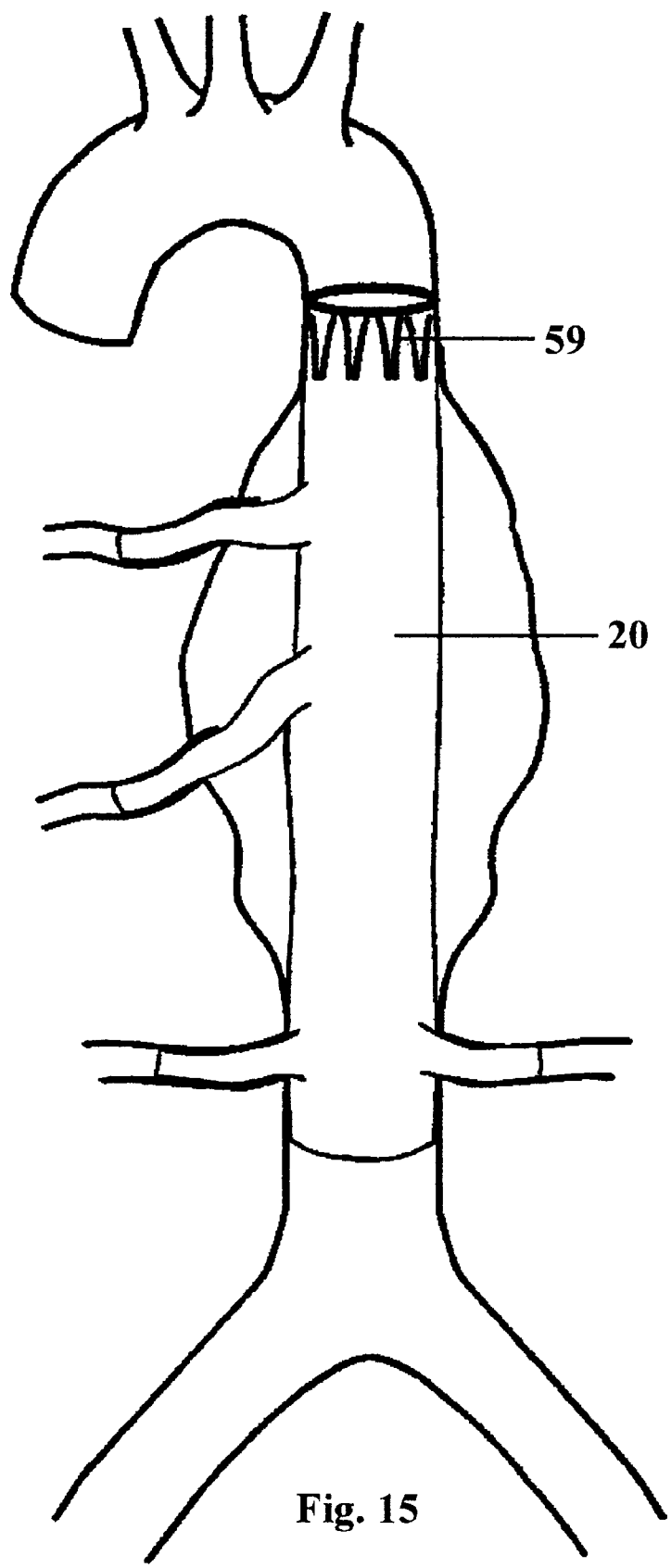
FIG. 15 is a perspective view of a stented graft deployed into the aorta and its branches.

In operation the present invention is comprised of the following steps. Under general anesthesia, the femoral artery, left and right brachial and left carotid arteries are exposed and controlled. Following heparinization and arteriotomy, guide wires 56 are passed into each brachiocephalic artery and retrieved into the femoral artery in the groin, as shown in FIG. 13. The graft 20 has strings 32 that are threaded through each branch and that attach to guide wires 56. The guide wires 56 have an attachment means such as a loop or the like (not shown) for attaching the strings 32 to the guide wires 56. In order to attach the strings 32, the guide wires 56 are passed through the femoral artery until the attachment means emerges. Once the attachment means emerges through the femoral artery, the strings 32 are tied to the guide wires 56 and then the strings 32 are retrieved out of the brachiocephalic arteries by means of the guide wires 56. After the strings 32 have been retrieved, one end of the graft 20 can be manipulated from the strings 32 extending out of the brachiocephalic arteries and the other end of the graft 20 can be manipulated from the other strings 32 that extend from the femoral artery. With the strings 32 attached at both ends of the graft 20, the graft 20 can be introduced into the femoral artery through a sheath (not shown). Once the graft 20 is introduced, it can be directed to the different branches of the aorta by manipulation of the strings 32 and the stylets 35. As shown in FIGS. 14 and 15, the several guide wires 56 can be used to position several branches of the graft 20 in the descending aorta. However, as shown in FIG. 7, the proximal end 26 of the graft 20 can be guided over the aortic arch to the ascending aorta by forward movement of the stylets 35.

In order to repair the aneurysm shown in FIGS. 14 and 15, the graft 20 is deployed to the descending aorta. Once the graft 20 is in position, the stents 59 are passed over the guide wires 56 by means of the stent catheter 62. The stents 59 are deployed into each of the branches of the graft 20 by the balloon catheter 62 and the aneurysm is excluded as shown in FIG. 15.

Figure 16:
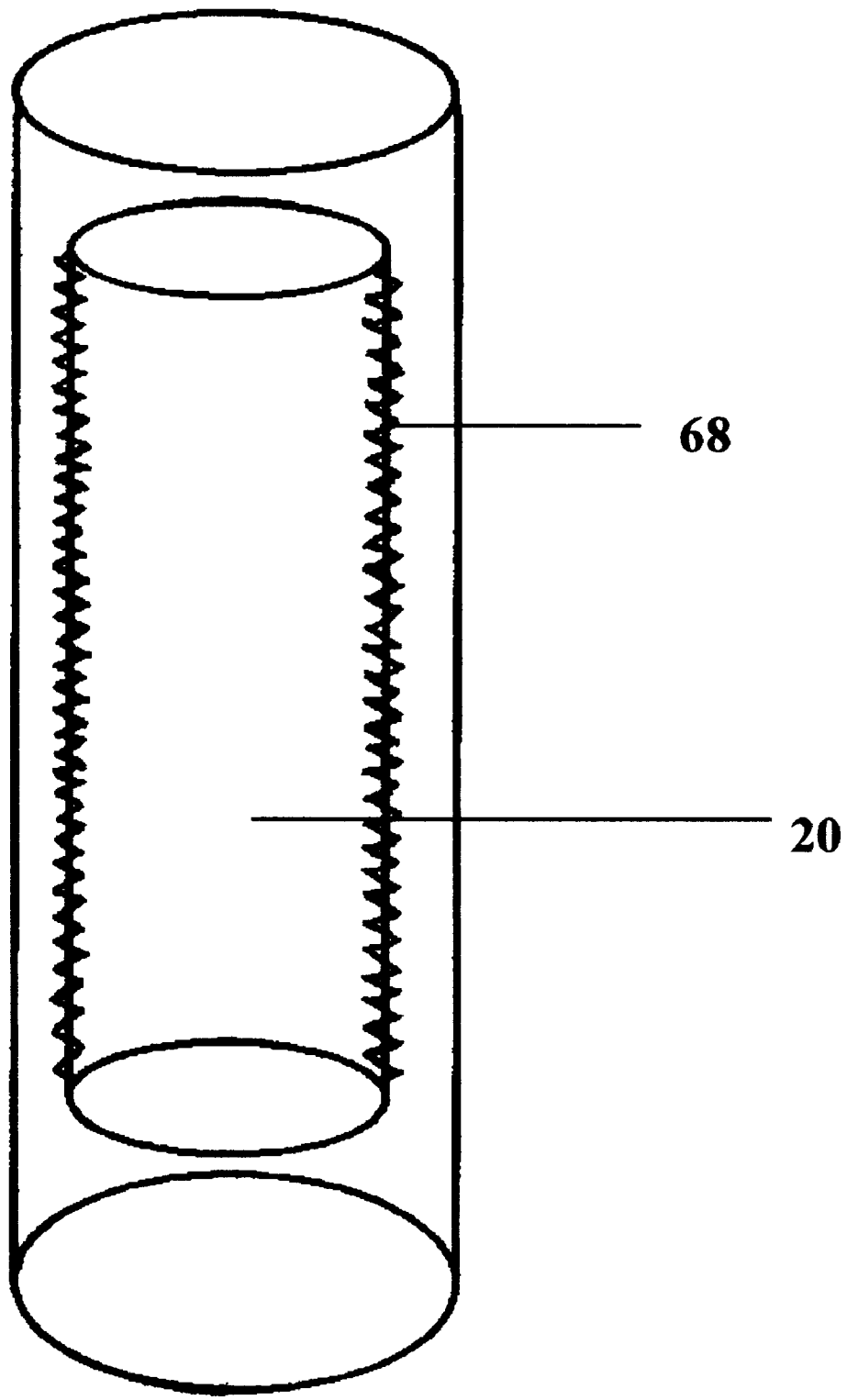
FIG. 16 is a perspective view of a graft positioned inside a vessel wall.

Turning to FIG. 16, the graft 20 is shown schematically inside an aortic wall 68. The graft 20 may be reinforced with an internal bar 71 (shown in FIGS. 17 and 18) that is preferably constructed of a radiopaque material and has prongs 74 at the proximal and distal ends. The internal bar 71 preferably has a diameter of approximately 1 mm and the prongs 74 extend approximately 3 mm at each end. The internal bar 71 prevents the graft 20 from bending to avoid leakage.

Figure 17:
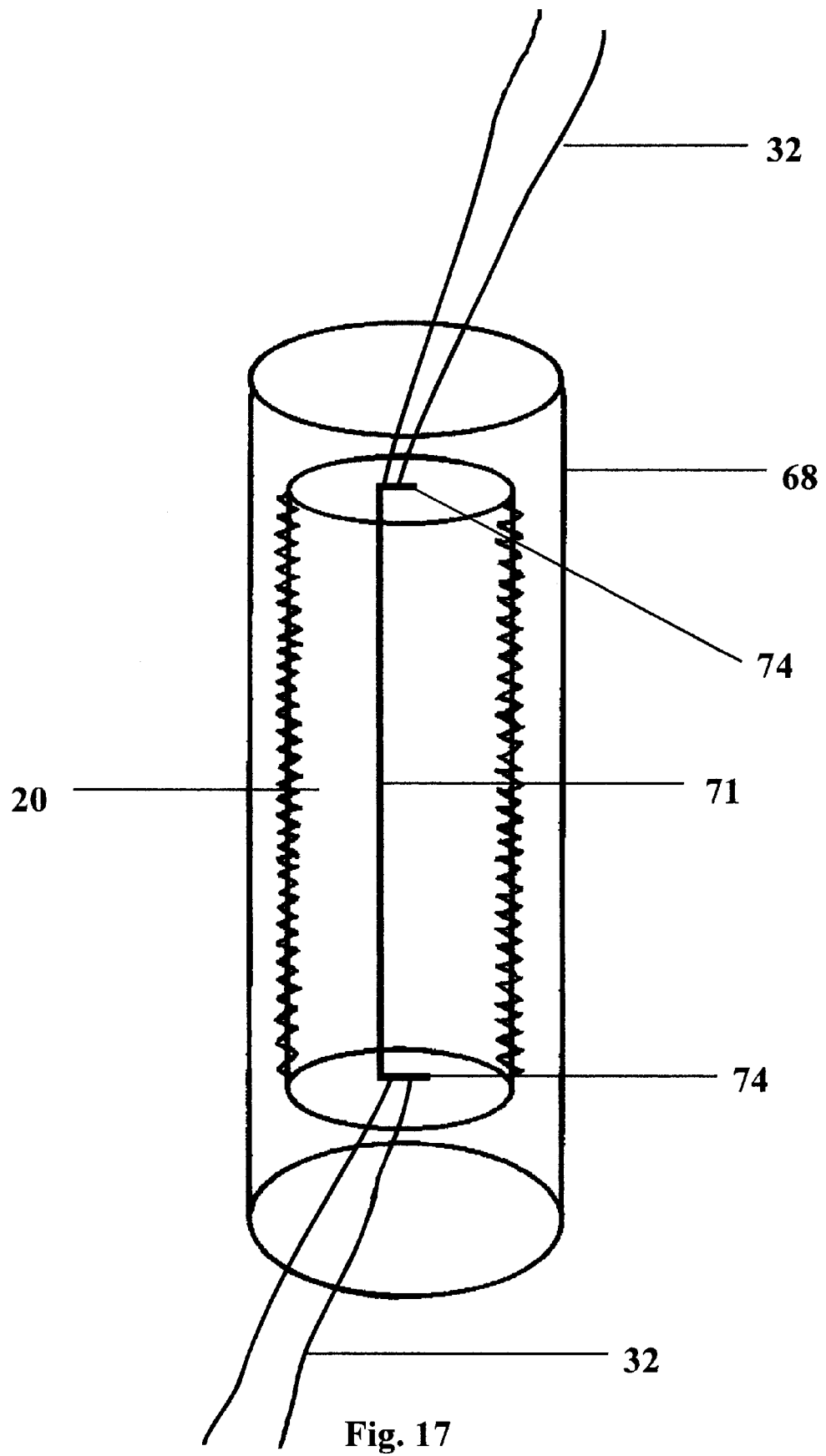
FIG. 17 is a perspective view of the internal bar of the present invention.
Figure 18:
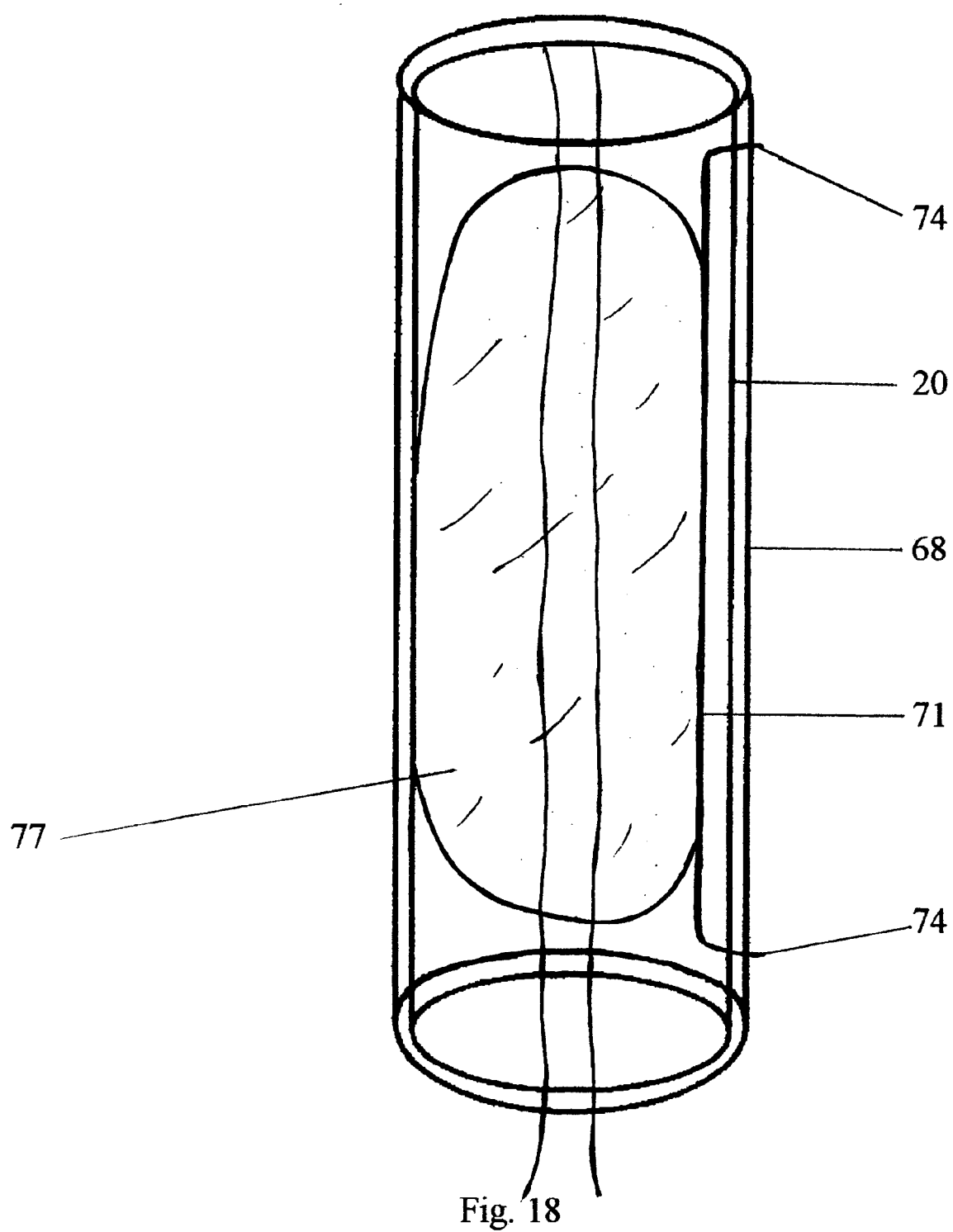
FIG. 18 is a perspective view of the internal bar of the present invention being deployed.

In FIG. 17 the internal bar 71 is brought to the desired location inside the graft 20 by means of the strings 32. In FIG. 18 a balloon catheter 77 is inflated inside the graft 20 and as a result pushes the bar 71 through the graft 20 into the aortic wall 68 to stabilize and prevent bleeding through the graft 20.

Figure 19:
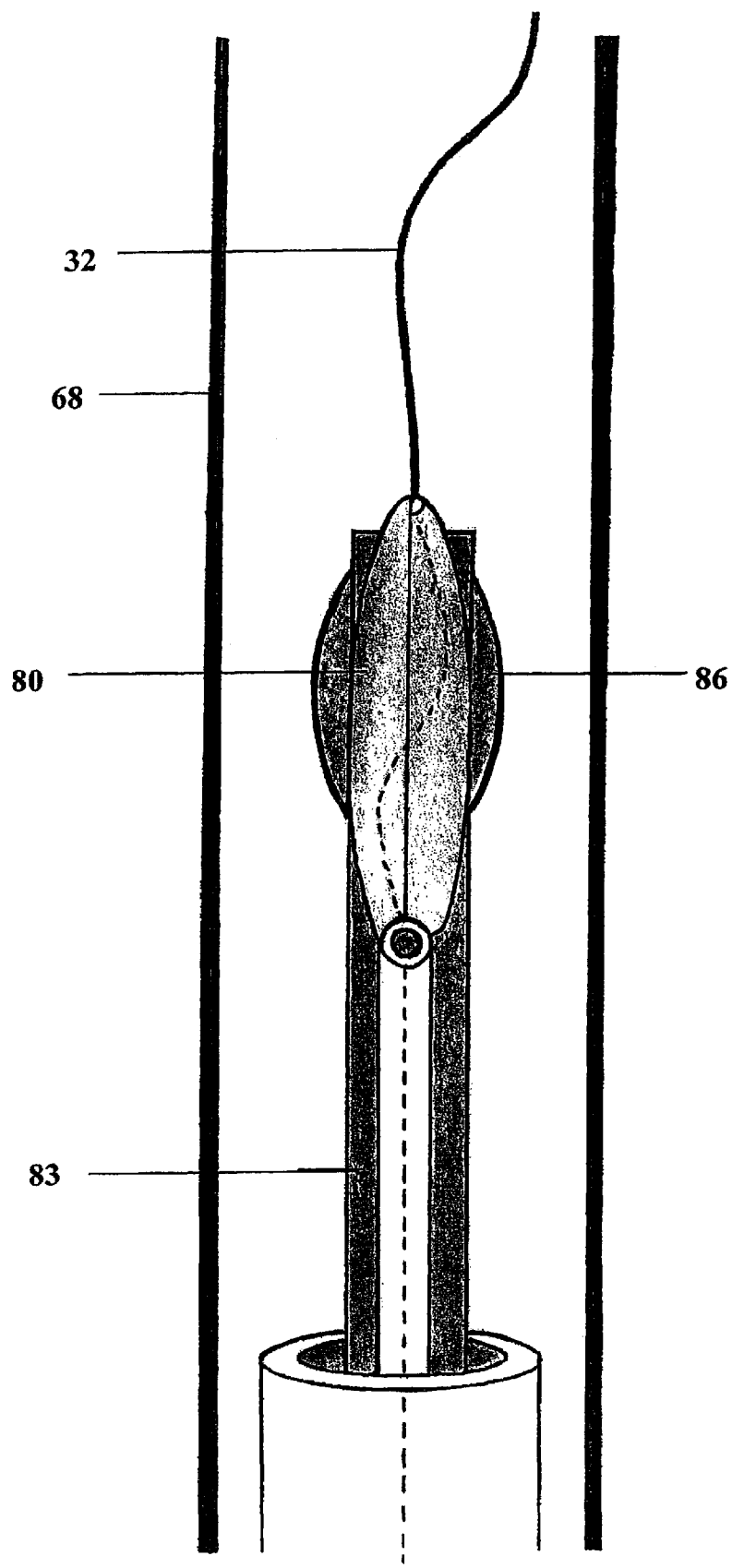
FIG. 19 is a perspective view of the endovascular scissors of the present invention guided by a thread.
Figure 20:
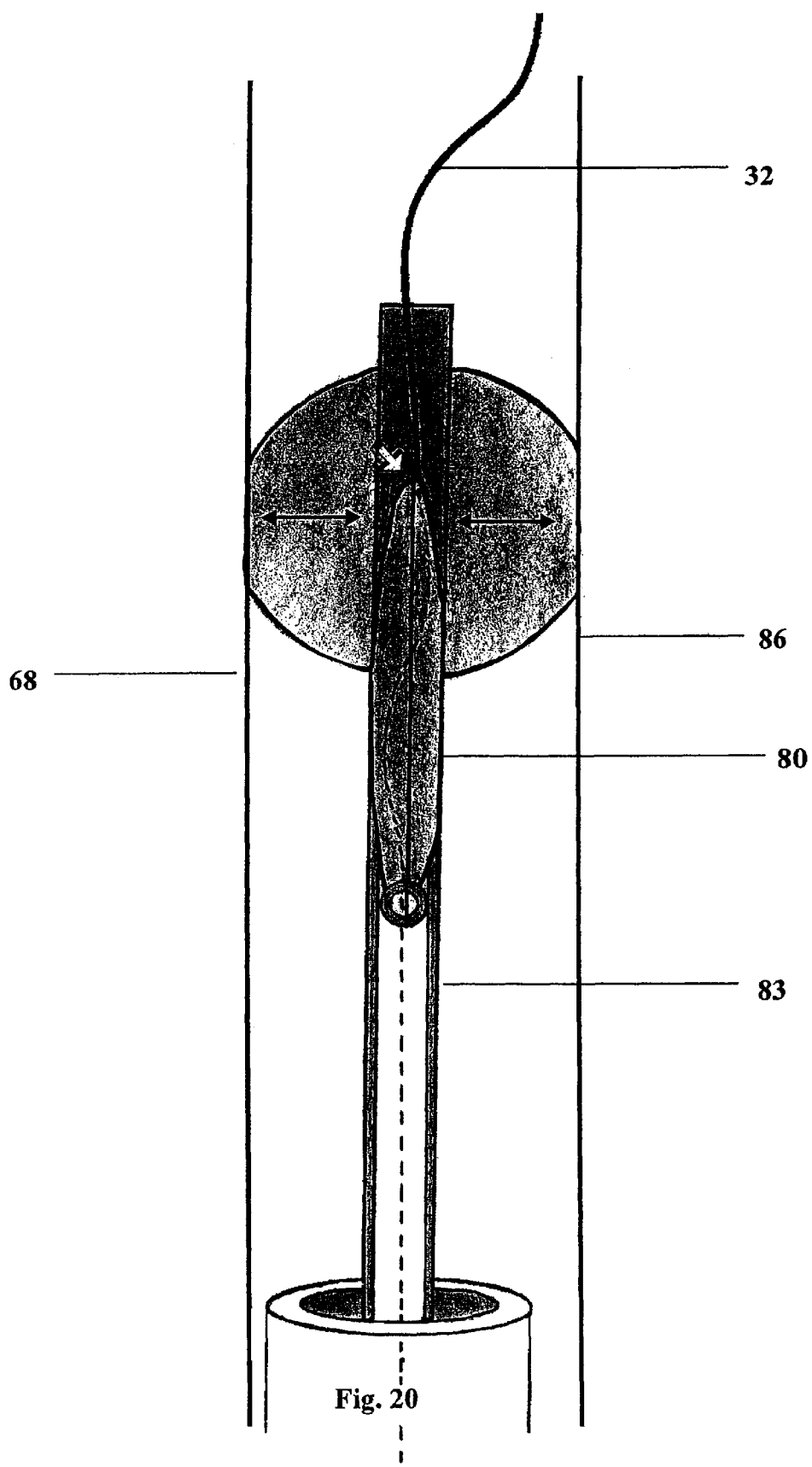
FIG. 20 is a perspective view of the endovascular scissors activated to cut the thread.
Figure 21:
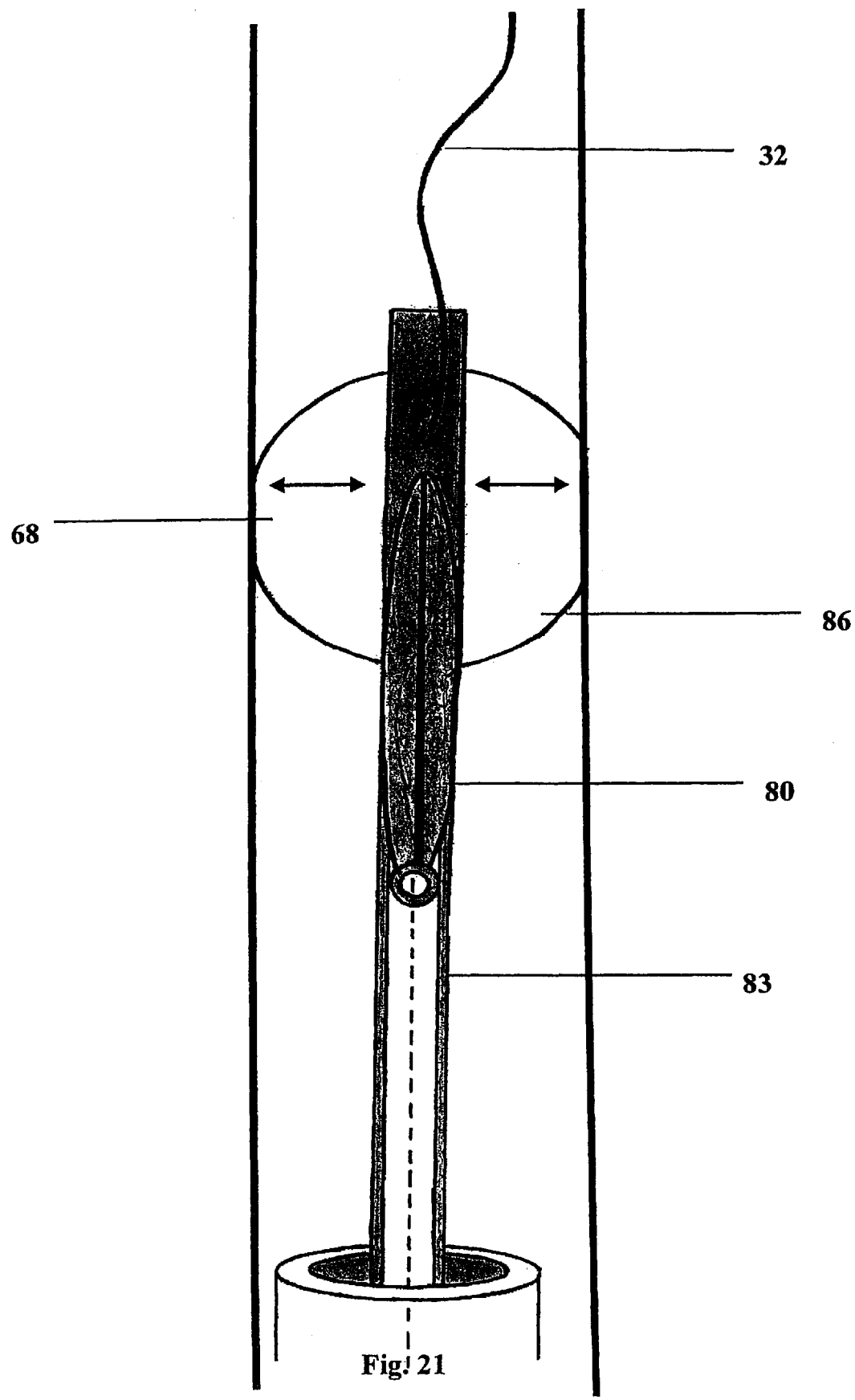
FIG. 21 is a perspective view of the endovasulcar scissors dividing the thread.

In FIGS. 19–21 endovascular scissors 80 provide for severing the strings 32 or guide wire 56 in order to facilitate removal of the strings 32 without disturbing the positioning of the graft 20. The scissors 80 are preferably deployed inside a catheter 83 that is disposed inside catheter 44 inside the aortic wall 68.

Turning to FIGS. 19 and 20, the catheter 83 has a balloon 86 attached. Accordingly, the catheter 83 is deployed along guide wire 56 and the balloon 86 can be inflated to open the vessel walls 68 or to deploy a stent 59 inside the graft 20. Inside catheter 83, the scissors 80 preferably have a flexible tip 89 for severing the guide wire 56 or strings 32.

For thoracoabdominal aneurysms a similar procedure is performed. However, insertion of guide wires 56 to celic, superior mesenteric, and renal arteries is required prior to introducing the graft 20 and deploying the stent 59.

The present invention provides several advantages, including the ability to efficiently and accurately position the graft 20 in the aortic arch and ascending aorta, as well as in the thoracoabdominal branches.

Another advantage is that the present invention provides a reduced cross-sectional area for percutaneous entry. The hydraulic stylet of the present invention is flexible and takes up a smaller cross-sectional area in its deflated state than conventional stylets and therefore can prevent damage to the arterial walls.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A graft assembly, comprising:
   a) a tubular graft having a central lumen extending to and meeting with first and second open ends;
   b) at least one string removably attached to the graft proximate the first open end; and
   c) at least one stylet having a length between distal and proximal ends, wherein the stylet is provided with an attachment portion at its distal end that captures the string adjacent to the first open end of the craft so that the proximal end of the stylet is manipulatable to move the distal end of the stylet and the graft connected to each other by the string to a treatment zone in a vasculature, and wherein the stylet and the string are detachable from the graft.

2. The graft assembly of claim 1, wherein the at least one stylet has an open loop as the attachment portion provided at the distal end of the stylet.

3. The graft assembly of claim 1, wherein there are a plurality of stylets disposed both outside the tubular graft and inside the central lumen.

4. The graft assembly of claim 1, wherein there is at least one inner stylet positionable through the central lumen of the graft with its distal end proximate the first open end of the graft and at least one outer stylet positionable outside the stylet with its distal end proximate the first open end of the graft, each of the inner stylet and the outer stylet having a loop at their respective distal ends as the attachment portion and wherein the at least one string extends through the loop of the inner stylet and through the loop of the outer stylet to attach the stylets to the graft.

5. The graft assembly of claim 1, wherein the at least one stylet is elongate and hollow.

6. The graft assembly of claim 5, wherein the at least one stylet is inflatable.

7. The graft assembly of claim 1, further comprising:
a catheter having a distal end and a proximal end, the proximal end of the catheter having at least one opening defined therein, wherein the catheter is attachable to the at least one string through the opening.

8. The graft assembly of claim 1, further comprising:
an internal bar having a length between first and second bar ends, wherein at least one of the first and second bar ends has a protrusion that is capable of being deployed through the graft into a vessel wall.

9. An apparatus for positioning a graft at a treatment zone in a vasculature, the apparatus comprising:
a) a tubular graft having a central lumen extending to and meeting with first and second open ends;
b) at least one first string removably attached to the graft proximate the first open end and at least one second string removable attached to the graft proximate the second open end;
c) at least one guide wire having a length sufficient to extend through the vasculature and past the treatment zone, wherein the guide wire has a proximal end manipulatable from a first location outside the vasculature and a distal end manipulatable from a second location outside the vasculater, the first and second locations outside the vasculature being on opposite sides of the treatment zone and wherein the guide wire has a first attachment portion at its proximal end that captures the first string adjacent to the first open end of the graft;
d) at least one stylet having a length between distal and proximal ends, wherein the stylet is provided with a second attachment portion at its distal end that captures the second string adjacent to the second open end of the graft so that the proximal end of the stylet is manipulatable to move the distal end of the stylet and the second open end of the craft connected to each other by the second string to the treatment zone in the vasculature as the distal end of the guide wire is manipulatable to move the proximal end of the guide wire and the first open end of the craft connected to each other by the first string to the treatment zone, and wherein the guide wire and the first string are detachable from the graft and the stylet and the second string are detachable from the graft.

10. The apparatus of claim 9, wherein the at least one stylet has an open loop as the attachment portion provided at the distal end of the stylet.

11. The apparatus of claim 9, wherein there are a plurality of stylets disposed both outside the tubular graft and inside the central lumen.

12. The apparatus of claim 9, wherein there is at least one inner stylet positionable through the central lumen of the graft with its distal end proximate the second open end of the graft and at least one outer stylet positionable outside the stylet with its distal end proximate the second open end of the graft, each of the inner stylet and the outer stylet having a loop at their respective distal ends as the attachment portion and wherein the at least one string extends through the loop of the inner stylet and through the loop of the outer stylet to attach the stylets to the graft.

13. The graft assembly of claim 9, wherein the at least one stylet is inflatable.

14. The graft assembly of claim 13, wherein the at least one stylet is elongate and hollow.

15. The apparatus of claim 9, further comprising:
a catheter having a distal end and a proximal end, the proximal end of the catheter having at least one opening defined therein, wherein the catheter is attachable to the at least one string through the opening.

16. The apparatus of claim 9, further comprising:
an internal bar having a length between first and second bar ends, wherein at least one of the first and second bar ends has a protrusion that is capable of being deployed through the graft into a vessel wall.

17. The apparatus of claim 9 further comprising:
endovascular scissors capable of being deployed by a catheter.

18. A method for engrafting a blood vessel to repair an aortic aneurysm comprising the steps of:
a) preloading a graft within a sheath introducer;
b) removably attaching a plurality of strings and a plurality of stylets to the graft;
c) inserting arterial sheaths into the brachiocephalic and femoral arteries percutaneously;
d) passing guide wires into the brachiocephalic arteries under an image amplifier;
e) retrieving first ends of said guide wires from the groin and attaching the plurality of strings to the guide wires;
f) pulling each guide wire from the femoral artery to the brachiocephalic artery;
g) withdrawing the guide wire from the brachiocephalic arteries;
h) removing the strings from the guide wires;
i) inserting the sheath introducer into the femoral artery;
j) guiding the graft to the location of the aortic aneurysm by pulling the strings and pushing the stylets;
k) holding the strings and stylets in position while removing the sheath introducer;
l) passing a preloaded stent catheter over said guide wires into a lumen of the graft;
m) deploying a stent into the graft;
n) withdrawing the stent catheter from the blood vessel and deploying another stent within the graft by the method of step m; and
o) removing the guide wires, the stent catheter, the strings, the stylets, and the arterial sheathes from the vessel and attending to the entry sites.

19. The method of claim 18, further comprising the step of pushing the graft from the aortic arch to the ascending aorta by pushing the stylet.

20. The method of claim 18, further comprising the step of providing an inflatable stylet.

21. The method of claim 20, further comprising the step of inflating the stylet.

22. The method of claim 18, further comprising the step of providing a catheter having a distal end and a proximal end, the proximal end having at least one opening defined therein, the catheter attached to the strings through the opening.

23. The method of claim 22, further comprising the step of pushing the graft over the aortic arch to the ascending aorta by pushing the proximal end of the catheter toward the ascending aorta.

24. The method of claim 18, further comprising the step of deploying an internal bar through the graft into a vessel wall.

25. The method of claim 18, further comprising the step of deploying endovascular scissors into the lumen through a catheter to cut the strings.

26. The apparatus of claim 9, including at least one stent capable of being deployed inside the graft.

27. The apparatus of claim 26 including a catheter capable of deploying the stent inside the graft.

28. A graft assembly, comprising:
   a) a tubular graft having a central lumen and a plurality of branches;
   b) a plurality of strings removably attached to the graft; and
   c) a plurality of inflatable stylets attached to the respective strings.

29. An apparatus for engrafting a blood vessel, the apparatus comprising:
   a) a tubular graft having a central lumen and a plurality of branches;
   b) a plurality of strings removably attached to the graft;
   c) a plurality of guide wires capable of attachment to the plurality of strings;
   d) a plurality of inflatable stylets attached to the respective strings;
   e) a plurality of stents capable of being deployed inside the graft; and
   f) a catheter capable of deploying the stent inside the graft.

30. An apparatus for engrafting a blood vessel, the apparatus comprising:
   a) a tubular graft having a central lumen and a plurality of branches;
   b) a plurality of strings removably attached to the graft;
   c) a plurality of guide wires capable of attachment to the plurality of strings;
   d) a plurality of stylets attached to the strings;
   e) a plurality of stents capable of being deployed inside the graft;
   f) a catheter capable of deploying the stent inside the graft; and
   g) endovascular scissors capable of being deployed by a catheter.

* * * * *